(12) United States Patent
Chien et al.

(10) Patent No.: US 8,506,783 B2
(45) Date of Patent: Aug. 13, 2013

(54) THREE-DIMENSIONAL NANOCHANNEL DEVICE AND METHOD OF MANUFACTURING THE SAME

(75) Inventors: Liang-Ju Chien, Kaohsiung (TW); Chi-Han Chiou, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 98 days.

(21) Appl. No.: 13/205,640

(22) Filed: Aug. 9, 2011

(65) Prior Publication Data

US 2012/0261263 A1 Oct. 18, 2012

(30) Foreign Application Priority Data

Apr. 14, 2011 (TW) .............................. 100112991 A

(51) Int. Cl.
*G01N 27/453* (2006.01)

(52) U.S. Cl.
USPC .......... 204/600; 204/601; 204/643; 977/962; 977/773; 977/707; 137/265; 137/255

(58) Field of Classification Search
USPC ................. 204/600, 601, 643; 977/707, 773, 977/962; 137/265, 255
See application file for complete search history.

(56) References Cited

U.S. PATENT DOCUMENTS

| | | | |
|---|---|---|---|
| 6,824,664 | B1 | 11/2004 | Austin et al. |
| 7,014,747 | B2 | 3/2006 | Cummings et al. |
| 7,204,923 | B2 | 4/2007 | Cummings |
| 7,678,256 | B2 | 3/2010 | Davalos et al. |
| 2004/0035701 | A1* | 2/2004 | Han et al. ..................... 204/451 |
| 2007/0039463 | A1* | 2/2007 | Desmet et al. ..................... 95/45 |
| 2010/0224493 | A1 | 9/2010 | Davalos et al. |

FOREIGN PATENT DOCUMENTS

TW 200940987 10/2009

OTHER PUBLICATIONS

N. Demierre et al, "Characterization and optimization of liquid electrodes for lateral dielectrophoresis", Lab on a Chip, The Royal Society of Chemistry 2007, Lab Chip, 2007, published on Dec. 21, 2006, p. 355-365.
H. Shafiee et al., "A Microfluidic System for Biological Particle Enrichment Using Contactless Dielectrophoresis", JALA, Jun. 2010, p. 224-232.
Lapizco-Encinas et al., "Dielectrophoretic Concentration and Separation of Live and Dead Bacteria in an Array of Insulators", Analytical Chemistry, vol. 76, No. 6, Mar. 15, 2004, p. 1571-p. 1579.
Chou et al., "Electrodeless Dielectrophoresis for Micro Total Analysis Systems", IEEE Engineering in Medicine and Biology Magazine, Nov./Dec. 2003, p. 62-p. 67.

* cited by examiner

*Primary Examiner* — J. Christopher Ball
*Assistant Examiner* — Jennifer Dieterle
(74) *Attorney, Agent, or Firm* — Jianq Chyun IP Office

(57) ABSTRACT

A three-dimensional nanochannel device and a method of manufacturing the same are provided. In the device, a first substrate, a second substrate, and a channel layer sandwiched by the first and the second substrates are included. At least one channel is constituted by the first and the second substrates and the channel layer and includes a fluid inlet, a fluid outlet, and at least one condensed channel between the fluid inlet and the fluid outlet. The condensed channel at least has a first size and a second size on an X-Y plane and has a third size and a fourth size on an X-Z plane. A difference between the first size and the second size is about at least two orders in scale, and a difference between the third size and the fourth size is about at least two orders in scale.

14 Claims, 13 Drawing Sheets

THREE-DIMENSIONAL NANOCHANNEL DEVICE AND METHOD OF MANUFACTURING THE SAME

CROSS-REFERENCE TO RELATED APPLICATION

This application claims the priority benefit of Taiwan application serial no. 100112991, filed Apr. 14, 2011. The entirety of the above-mentioned patent application is hereby incorporated by reference herein and made a part of this specification.

TECHNICAL FIELD

The disclosure relates to a three-dimensional nanochannel device and a method of manufacturing the same.

BACKGROUND

In March 2010, the Health Care and Education Reconciliation Act was passed in the United States, and personalized health care was included in this Act. The testing of biomarkers is one of the key technologies in personalized healthcare. Currently, concentrations of biomarkers range from $10^1$ to $10^{-12}$ mg/mL (ppt), including as high as 13 orders of magnitude. For thousands of testing procedures, each of them should be completed with 50-500 nanoliters (nL) of blood plasma; in such volumes, the numbers of molecules which have very low concentrations are relatively rare. However, for the testing of low-concentration samples, the volumes of the specimens is too little to become invalid samples. Therefore, a microchannel which is able to both contain sufficient samples and rapidly concentrate biomarkers is important for testing.

Dielectrophoresis is a kind of method to effectively concentrate protein.

However, dielectrophoresis with metal electrode has problems such as electrode hydrolysis, low concentration efficiency, and generation of joule heat. In recent years, electrode-less dielectrophoresis has been developed to resolve the problems in dielectrophoresis with metal electrode. According to the dielectrophoresis equation ($F_{DEP}=2\pi a^3 \epsilon_m Re(K^*(\omega))\nabla E^2$), in order to generate enough dielectrophoretic force, a great enough electric field gradient is required. Electrode-less dielectrophoresis mainly uses a structural design to generate a condensed electric field. There are different designs such as a rectangle, a column, and a triangle. The use of a design of a triangular condensed structure which is able to completely concentration the sample at a structural limiting space is the most efficient condensing method. However, since a nanostructure is manufactured by electron beam lithography, when used in conjunction with a channel about 100 nm deep, a reaction volume is only at the picoliter (pL) level. The molecular sizes of some biomarkers are about several tens of nanometers. However, in such low reaction volumes, for the testing of very low concentrations, the number of molecules included in such volumes are relatively reduced, even to zero.

SUMMARY

A three-dimensional nanochannel device is introduced herein. The three-dimensional nanochannel device includes a second substrate, a first substrate, and a channel layer, and the channel layer is sandwiched by the first substrate and the second substrate. At least one channel is constituted by the first and the second substrates and the channel layer and includes a fluid inlet, a fluid outlet, and at least one condensed channel between the fluid inlet and the fluid outlet. The condensed channel at least has a first size and a second size on an X-Y plane and has a third size and a fourth size on an X-Z plane. A difference between the first size and the second size is about at least two orders in scale, and a difference between the third size and the fourth size is about at least two orders in scale.

A method of manufacturing a three-dimensional nanochannel device is further introduced herein. In the method, a first insulation layer is formed on a substrate, a first opening is formed in the first insulation layer, and a patterned photoresist is formed on the first insulation layer. The patterned photoresist includes at least one second opening, wherein the second opening is adjacent to the first opening and exposes the first insulation layer. Afterwards, the first insulation layer is etched and the substrate is also continued to be etched by using the patterned photoresist as a mask, so as to form a housing space, wherein a depth of the housing space is at least two orders greater than a thickness of the first insulation layer. Thereafter, the patterned photoresist is removed, and a second insulation layer is formed on a surface of the substrate.

A method of manufacturing a three-dimensional nanochannel device is yet introduced herein. In the method, a silicon chip is etched to form a condensed channel because different lattice planes have different etch rates. The sizes of the condensed channel on the X-Y plane and the X-Z plane are shrunken at least two orders in scale. The above silicon chip and the first substrate and the second substrate are then assembled.

In order to make the aforementioned and other objects, features and advantages of the disclosure comprehensible, embodiments accompanied with figures are described in detail below.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1A:
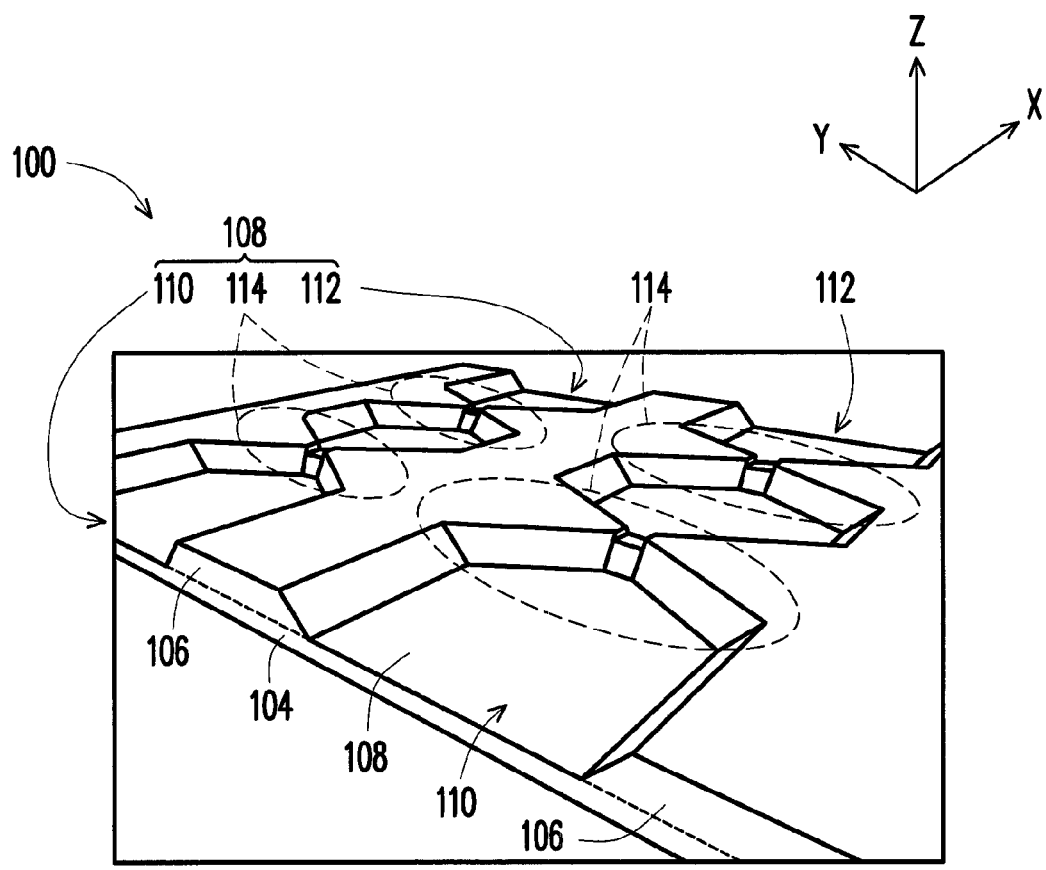
FIG. 1A is schematic three dimensional diagram of a three-dimensional nanochannel device according to an exemplary embodiment.

In the following description, please refer to the accompanying drawings, so that the embodiments of the disclosure may be illustrated more fully. However, the disclosure may be implemented in multiple different manners and is not limited to the embodiments described herein. In addition, for the sake for clarity, sizes or relative sizes of layers and areas shown in the drawings may not be drawn to scale.

Figure 1B:
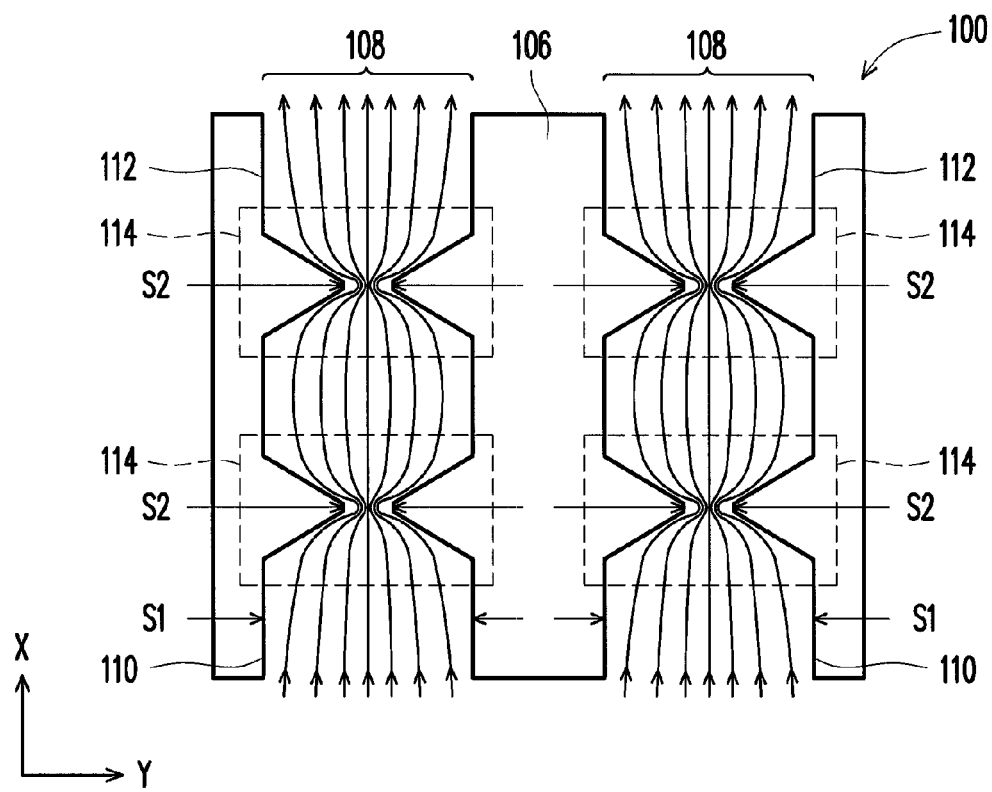
FIG. 1B is a schematic top diagram of a channel layer of FIG. 1A on an X-Y plane.
Figure 1C:
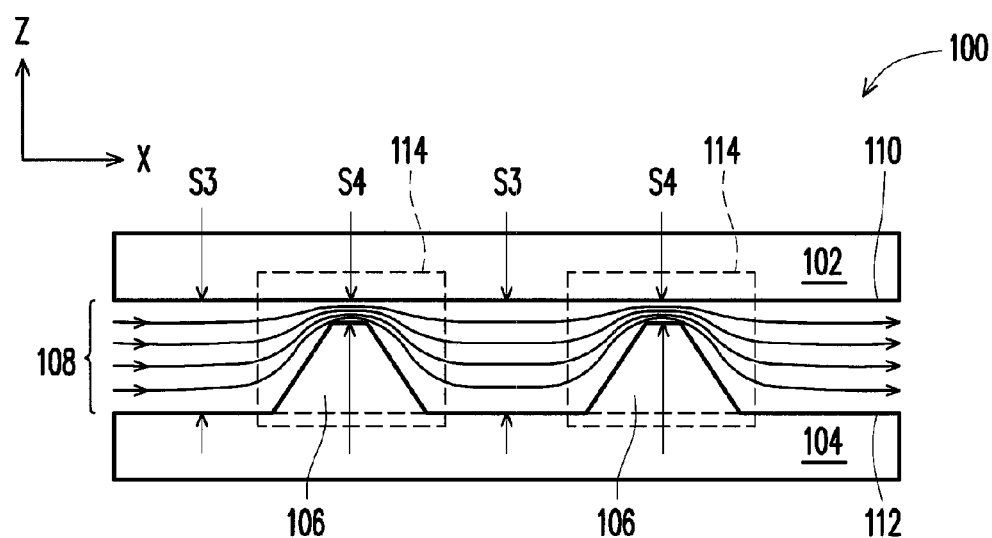
FIG. 1C is a schematic cross-sectional diagram of the three-dimensional nanochannel device of FIG. 1A on an X-Z plane.

FIG. 1A is schematic three dimensional diagram of a three-dimensional nanochannel device according to an exemplary embodiment. FIG. 1B is a schematic top diagram of a channel layer of FIG. 1A on an X-Y plane. FIG. 1C is a schematic cross-sectional diagram of the three-dimensional nanochannel device of FIG. 1A on an X-Z plane.

Please refer to FIGS. 1A-1C. A three-dimensional nanochannel device 100 according to the exemplary embodiment includes a second substrate 102, a first substrate 104, and a channel layer 106 sandwiched by the second and the first substrates 102 and 104. A channel 108 is constituted by the first and the second substrates 102 and 104 and the channel layer 106. In FIGS. 1A-1C, two channels 108 are shown. Each channel 108 includes a fluid inlet 110, a fluid outlet 112, and two condensed channels 114 between the fluid inlet and outlet 110 and 112. Hence, in this exemplary embodiment, four condensed channels 114 are shown. The condensed channel 114 at least has a first size S1 and a second size S2 on an X-Y plane and has a third size S3 and a fourth size S4 on an X-Z plane. A difference between the first size S1 and the second size S2 is about at least two orders in scale, and a difference between the third size S3 and the fourth size S4 is about at least two orders in scale. For example, the profile of each condensed channel 114 on the X-Y plane may be gradually shrunken from the first size S1 of several hundreds of micrometers to the second size S2 of several hundreds of nanometers (as shown in FIG. 1B), so that an electric field is condensed. The profile of each condensed channel 114 on the X-Z plane may be gradually shrunken from the third size S3 of several hundreds of micrometers to the fourth size S4 of several tens of nanometers (as shown in FIG. 1C), so that the electric field is further condensed to a condensed electric field as high as $10^7$ V/m. A reactive volume is further increased to the nanoliter (nL) level, so that a sufficient number of molecules is provided for detection.

Figure 2A:
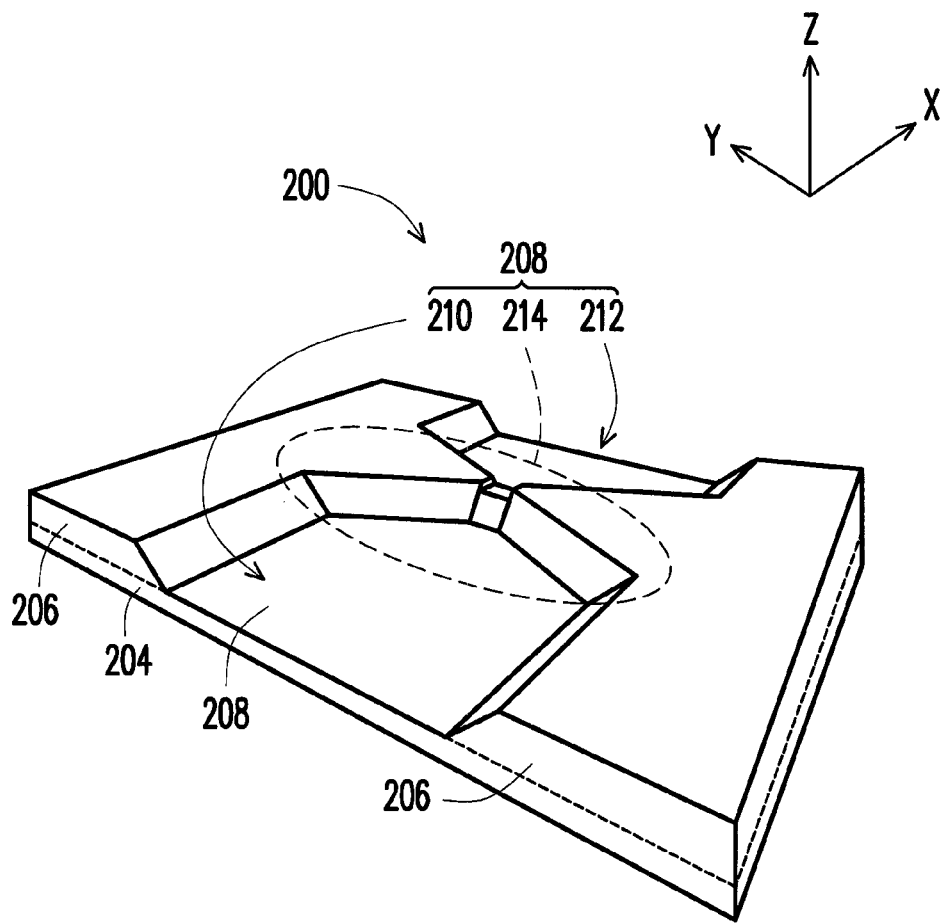
FIG. 2A is schematic three dimensional diagram of a three-dimensional nanochannel device according to another exemplary embodiment.
Figure 2B:
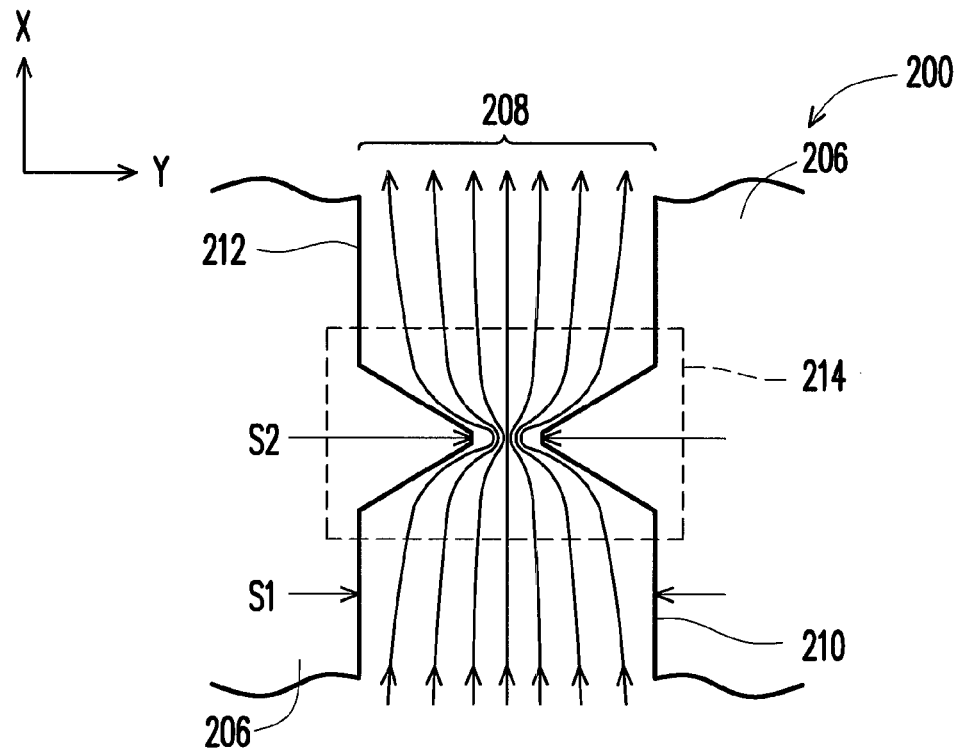
FIG. 2B is a schematic top diagram of a channel layer of FIG. 2A on an X-Y plane.
Figure 2C:
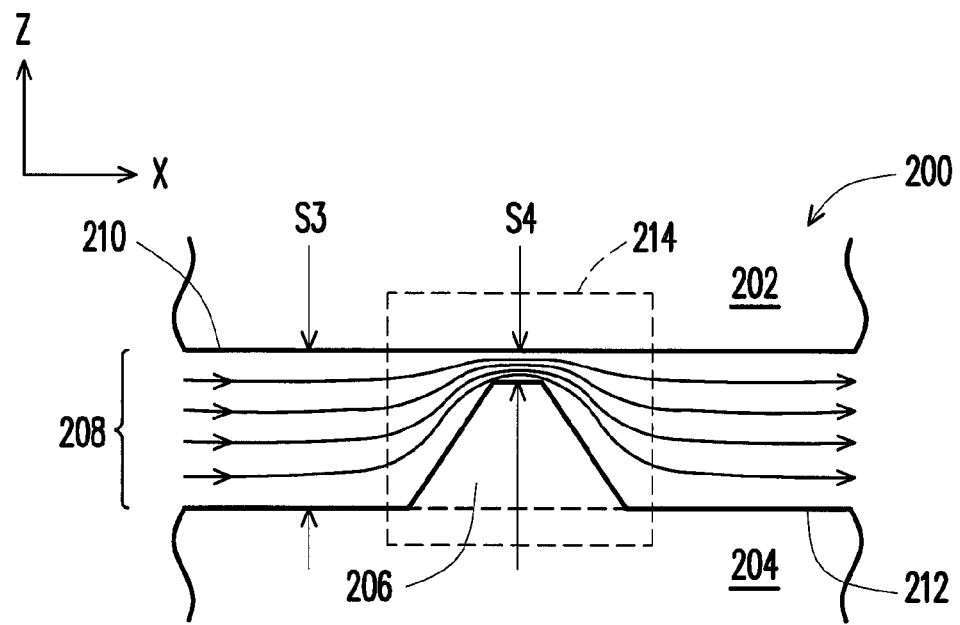
FIG. 2C is a schematic cross-sectional diagram of the three-dimensional nanochannel device of FIG. 2A on an X-Z plane.

FIG. 2A is schematic three dimensional diagram of a three-dimensional nanochannel device according to another exemplary embodiment. FIG. 2B is a schematic top diagram of a channel layer of FIG. 2A on an X-Y plane. FIG. 2C is a schematic cross-sectional diagram of the three-dimensional nanochannel device of FIG. 2A on an X-Z plane.

Please refer to FIGS. 2A-2C. A three-dimensional nanochannel device 200 according to the exemplary embodiment includes a second substrate 202, a first substrate 204, and a channel layer 206 sandwiched by the second and the first substrates 202 and 204. A channel 208 is constituted by the first and the second substrates 202 and 204 and the channel layer 206. In FIGS. 2A-2C, one channel 208 is shown, and the channel 208 includes a fluid inlet 210, a fluid outlet 212, and one condensed channel 214 therebetween. The condensed channel 214 at least has a first size S1 and a second size S2 on an X-Y plane and has a third size S3 and a fourth size S4 on an X-Z plane. A difference between the first size S1 and the second size S2 is about at least two orders in scale, and a difference between the third size S3 and the fourth size S4 is about at least two orders in scale. For example, the profile of the condensed channel 214 on the X-Y plane may be gradually shrunken from the first size S1 of several hundreds of micrometers to the second size S2 of several hundreds of nanometers (as shown in FIG. 2B). The profile of the condensed channel 214 on the X-Z plane may be gradually shrunken from the third size S3 of several hundreds of micrometers to the fourth size S4 of several tens of nanometers (as shown in FIG. 2C), so that the electric field is condensed to a condensed electric field as high as $10^7$ V/m. A reactive volume is further increased to the nanoliter (nL) level, so that a sufficient number of molecules is provided for detection.

Moreover, the three-dimensional nanochannel device according to above exemplary embodiments may be manufactured by any suitable process. In point of manufacturing costs, the device may be fabricated by the following method.

FIGS. 3A-3G are schematic diagrams showing a method of manufacturing the three-dimensional nanochannel device in FIG. 1.

Figure 3A:
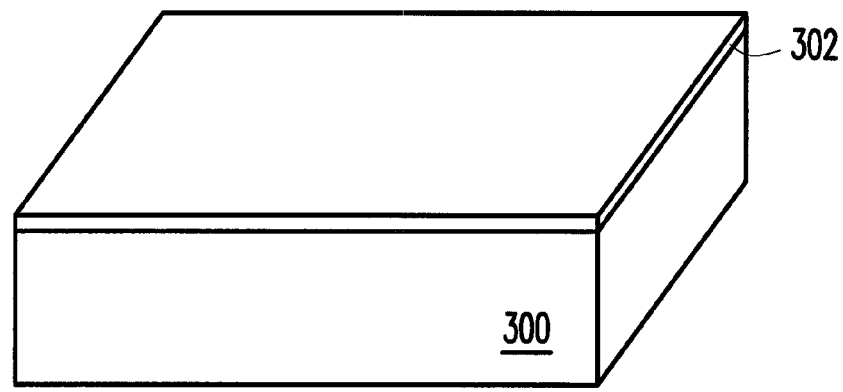
FIGS. 3A-3G are schematic diagrams showing a method of manufacturing the three-dimensional nanochannel device in FIG. 1.

First, a substrate 300 such as a silicon chip is provided, and an insulation layer 302 of an oxide layer which is, for example, several hundred nanometers thick is deposited on the substrate, as shown in FIG. 3A.

Figure 3B:
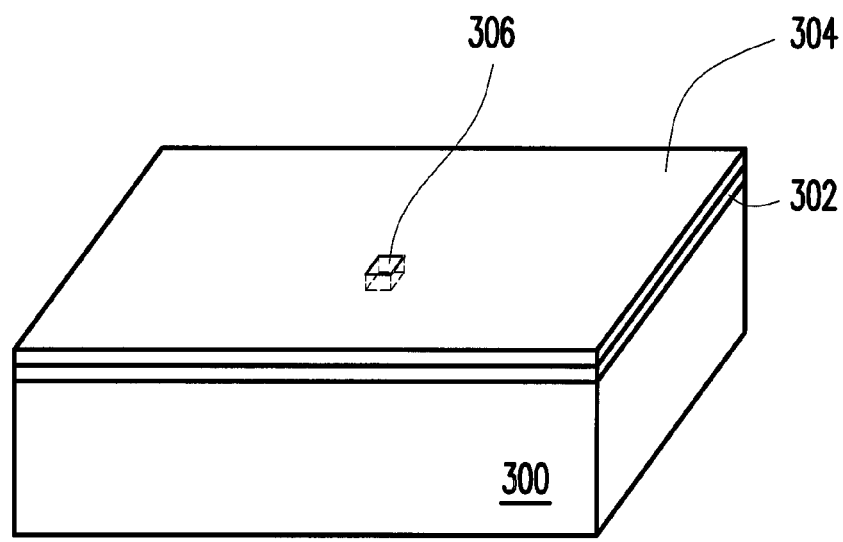

Next, please refer to FIG. 3B. An opening is formed in the insulation layer 302. The detailed steps include, for example, forming a patterned photoresist 304 using yellow light lithography and developing processes. At this moment, a part of the insulation layer 302 is exposed from an opening 306. This opening 306 corresponds to a position of the second size S2 in FIG. 1B.

Figure 3C:
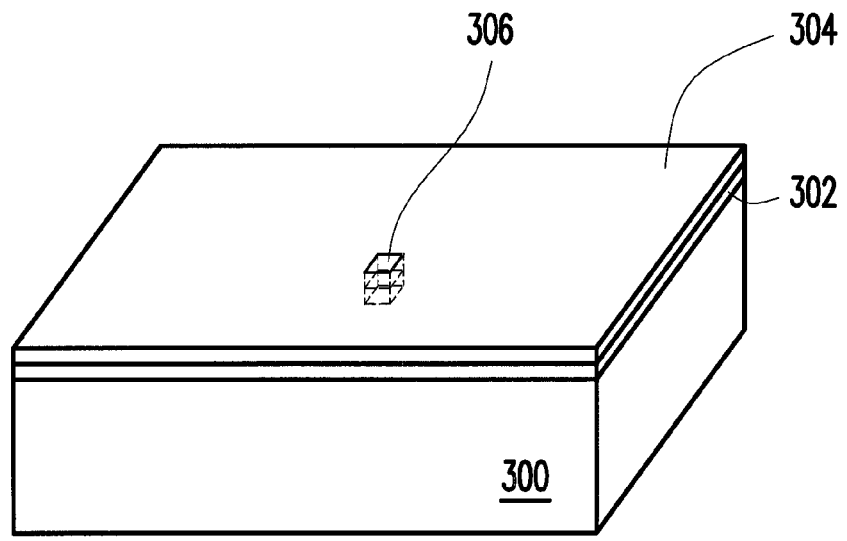

Next, please refer to FIG. 3C. By using the patterned photoresist 304 as a mask, the insulation layer 302 is etched until the substrate 300 in the opening 306 is exposed.

Figure 3D:
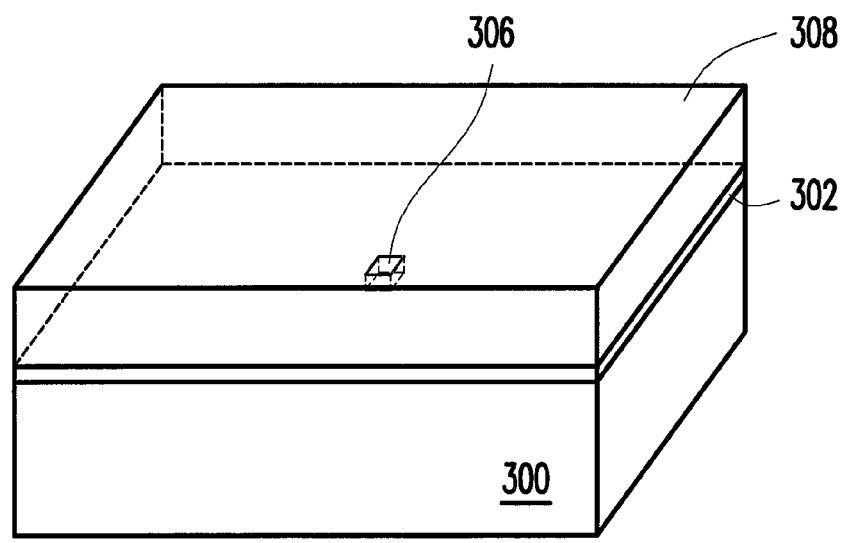

Next, please refer to FIG. 3D. The patterned photoresist 304 is completely removed, so that the insulation layer 302 which includes the opening 306 is obtained. Afterwards, another full layer of photoresist 308 is additionally formed on the substrate 300 and the insulation layer 302.

Figure 3E:
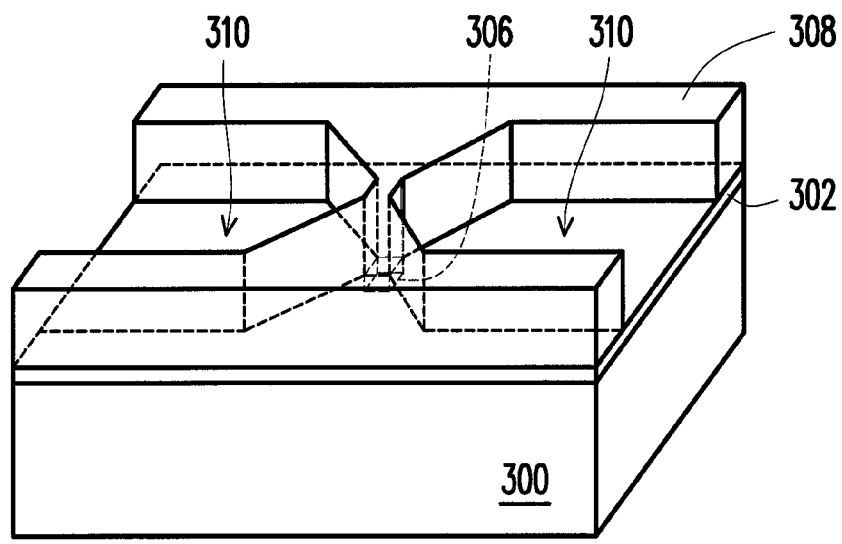

Next, please refer to FIG. 3E. The photoresist 308 is patterned by using yellow light lithography and developing processes, so as to form another patterned photoresist, and a part of the insulation layer 302 is exposed from openings 310. The openings 310 corresponding to the positions of the first size S1 in FIG. 1B and are adjacent to the opening 306.

Figure 3F:
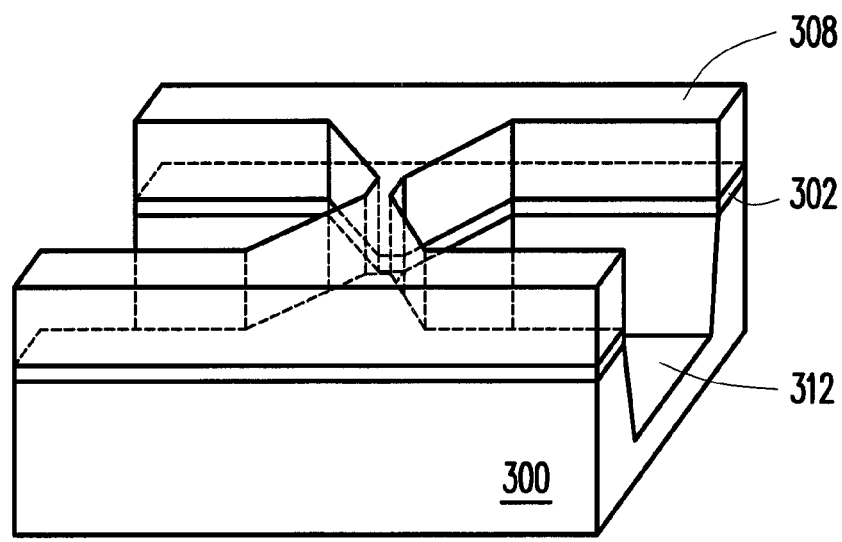

Next, as shown in FIG. 3F, the insulation layer 302 and the substrate 300 below are etched by using the photoresist 308 as a mask until a depth of a housing space 312 is near the third size S3 in FIG. 1C is formed in the substrate 300. At this moment, the depth of the housing space 312 is at least two orders greater than the thickness of the insulation layer 302.

Figure 3G:
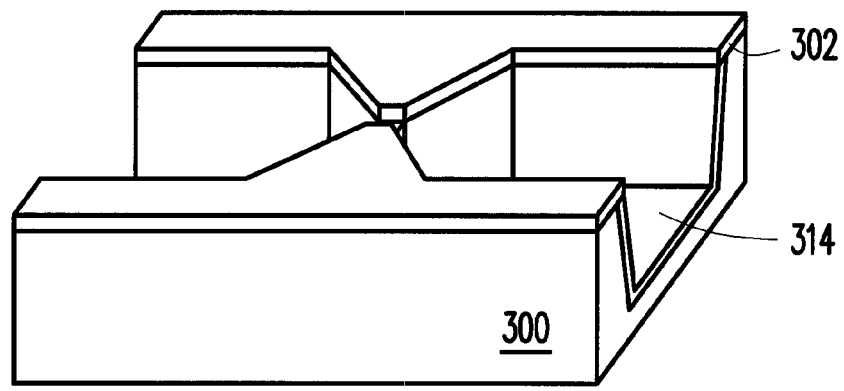

Then, please refer to FIG. 3G. After the photoresist 308 is removed, in order to make the structure insulating, an insulation layer 314 whose thickness achieves insulation may be further deposited on the exposed surface of the substrate 300, so as to function as an insulation surface.

The above processes only describes one of the methods of manufacturing the three-dimensional nanochannel device 100 in FIG. 1. However, the disclosure is not limited to this process.

Moreover, a number, a shape, and an arrangement of the channel 108 and a number and a shape of the condensed channel 114 of the three-dimensional nanochannel device may all be altered, as long as the sizes on the X-Y plane and the X-Z plane are both reduced. By utilizing three dimensional channel designs, the electric field generates a regional high electric field greater than a conventional 2D device, thereby achieving the purpose of fixed-amount concentration.

For example, in FIG. 1, there are four condensed channels 114, in which the profile are reduced on the X-Y plane and are then reduced on the X-Z plane.

Figure 4A:
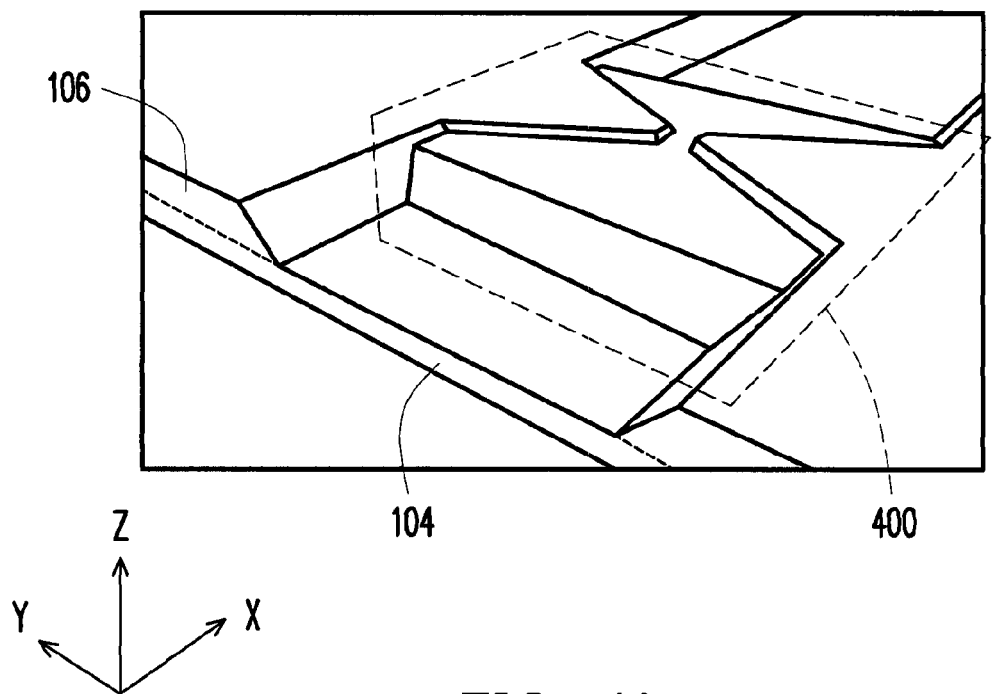
FIGS. 4A and 4B show two examples of the condensed channel in the three-dimensional nanochannel device according to above exemplary embodiment.
Figure 4B:
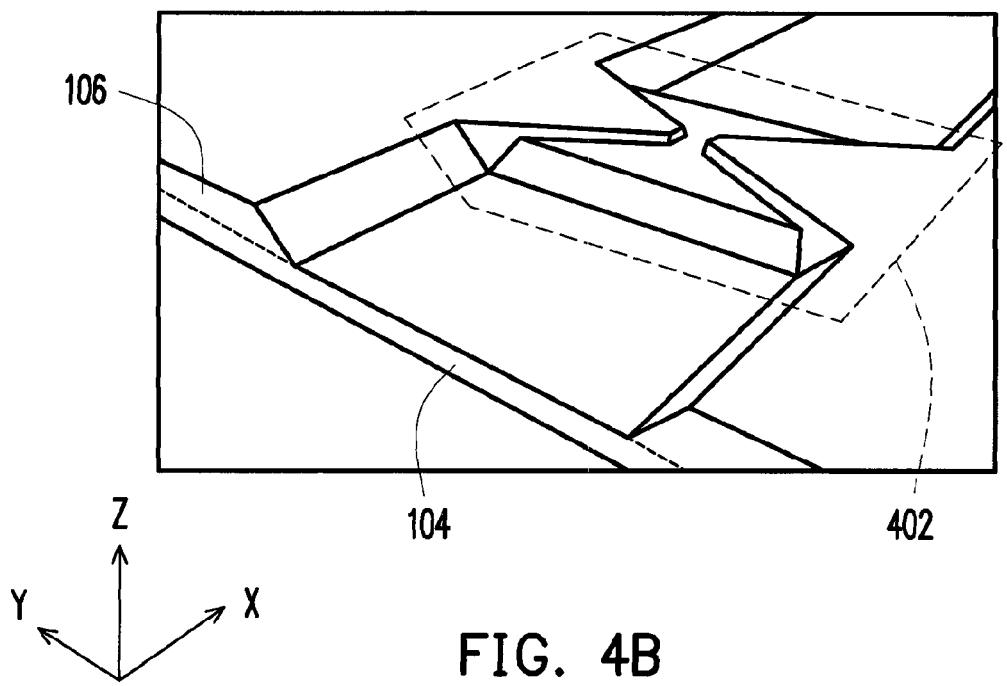

In the condensed channel 400 shown in FIG. 4A, the profile on the X-Z plane is reduced and then the profile on the X-Y plane is reduced. In the condensed channel 402 shown in FIG. 4B, the profiles on the X-Z plane and the profile on the X-Y plane are reduced simultaneously.

Moreover, the positions where the condensed channels 114 in the three-dimensional nanochannel device 100 have the smallest sizes are between the channel layers 106 and the second substrate 102, as shown in FIG. 1C. However, the disclosure is not limited to this configuration. For example, positions 500 where the condensed channels 114 in the three-dimensional nanochannel device 100 have the smallest sizes may be inside the channel layer 106 (as shown in FIG. 5A), or positions 502 where the condensed channels 114 in the three-dimensional nanochannel device 100 have the smallest sizes may be between the channel layer 106 and the first substrate 104 (as shown in FIG. 5B).

Figure 5A:
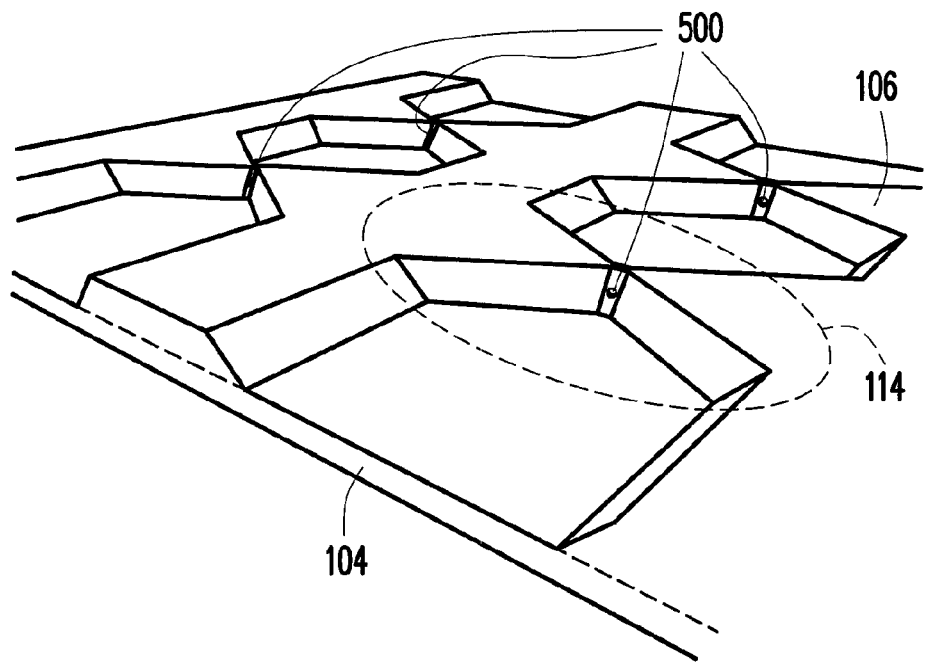
FIGS. 5A and 5B show two examples of positions where the condensed channel in the three-dimensional nanochannel device according to above exemplary embodiment has the smallest size.
Figure 5B:
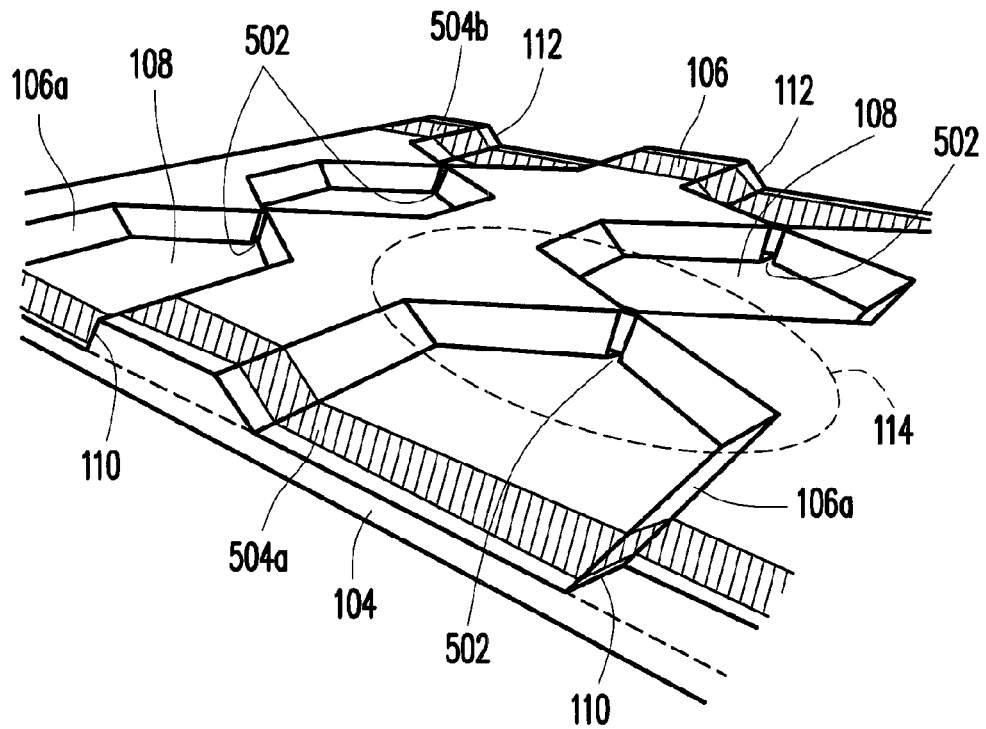

FIG. 5A further shows a first electrode 504a and a second electrode 504b. These electrodes 504a and 504b are respectively disposed on the channel layer 106 of and the first substrate 104 at the fluid inlet 110 and the fluid outlet 112 in a direction perpendicular to the channel 108. In order that the electrodes 504a and 504b do not easily break during disposition, sidewalls 106a of the channel layer 106 may be sloped, for example. Alternatively, the electrodes 504a and 504b may be disposed at positions outside the channel 108.

Figure 6A:
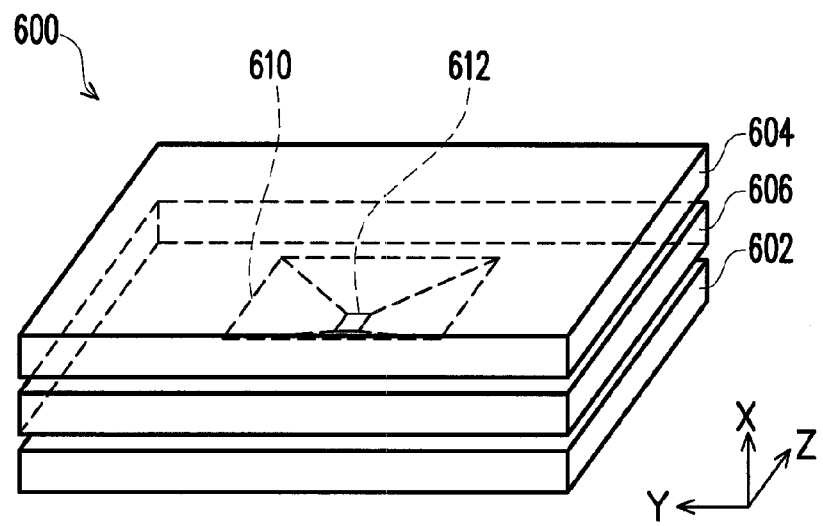
FIG. 6A is schematic three dimensional diagram of a three-dimensional nanochannel device according to yet another exemplary embodiment.
Figure 6B:
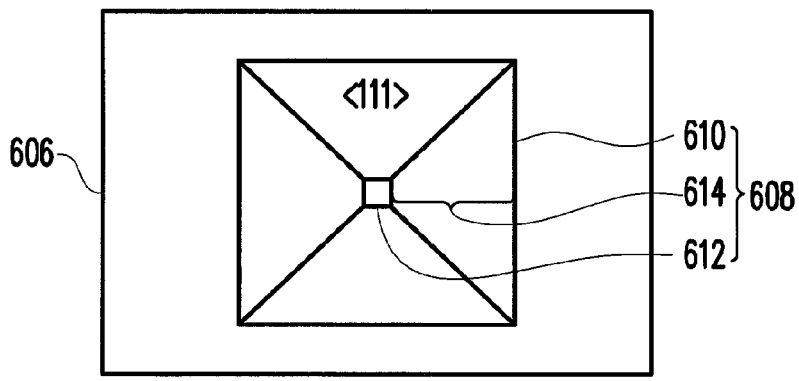
FIG. 6B is a schematic top diagram of a Y-Z plane of FIG. 6A.
Figure 6C:
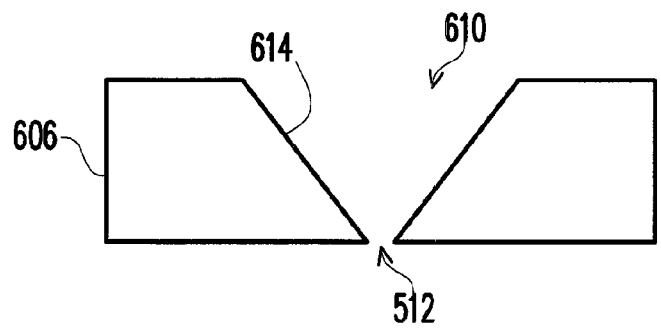
FIG. 6C is a schematic cross-sectional diagram of an X-Y plane (or X-Z plane) of FIG. 6A.

FIG. 6A is schematic three dimensional diagram of a three-dimensional nanochannel device according to yet another exemplary embodiment; FIGS. 6B and FIG. 6C are respectively a schematic top diagram of a Y-Z plane and a schematic cross-sectional diagram of an X-Y plane (or X-Z plane) of a channel layer in FIG. 6A.

Please refer to FIGS. 6A-6C. A three-dimensional nanochannel device 600 according to this exemplary embodiment includes a first substrate 602, a second substrate 604, and a channel layer 606 sandwiched by the first and the second substrates 602 and 604. A channel 608 is constituted by the first and the second substrates 602 and 604 and the channel layer 606. The channel 608 includes a fluid inlet 610, a fluid outlet 612, and a condensed channel 614 between the fluid inlet and outlet 610 and 612. When the channel layer 606 is a silicon chip, the condensed channel 614 is easily fabricated by utilizing an etching process because lattice planes of the silicon chip have different etch rates. For example, since the lattice plane (111) has a lower etch rate than the lattice plane (110), the condensed channel 614 in FIG. 6B may be completed by single wet etching process. The sizes of the condensed channel 614 on an X-Y plane and an X-Z plane are shrunken at least two orders in scale, such as being shrunken from the millimeter level to the micrometer level.

Figure 7:
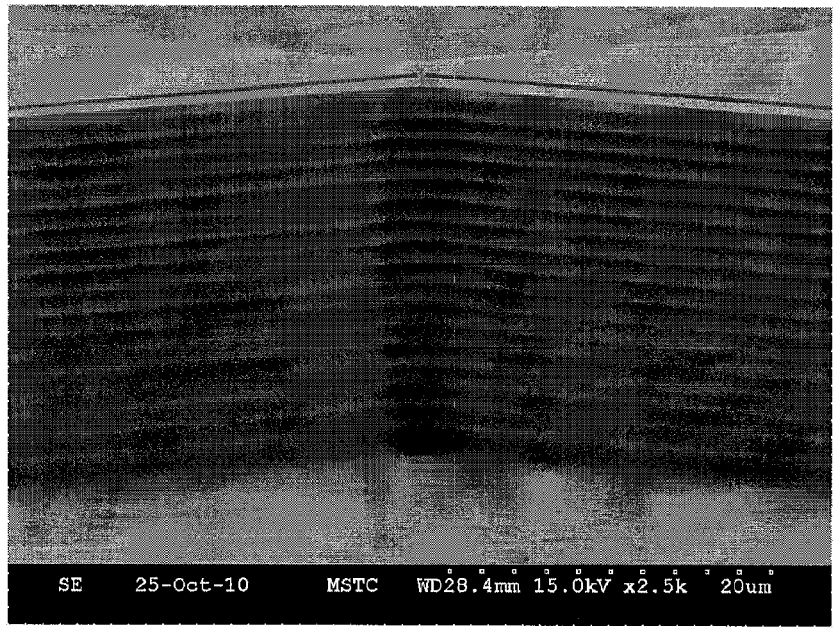
FIG. 7 is a scanning electron microscope (SEM) photograph of the condensed channel of the three-dimensional nanochannel device.
Figure 8:
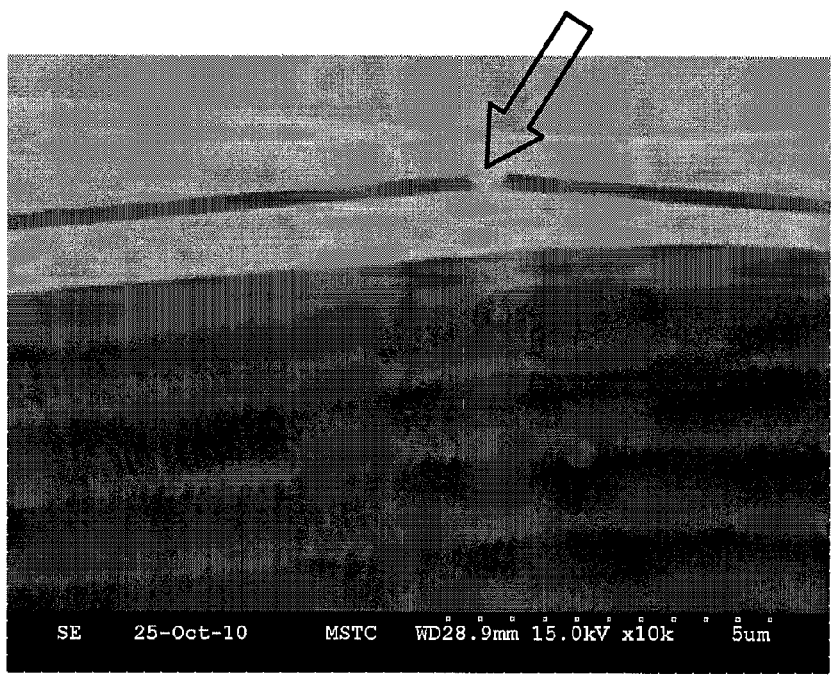
FIG. 8 is an SEM photograph of FIG. 7 which is magnified to four times.

FIG. 7 is a scanning electron microscope (SEM) photograph of the condensed channel of the three-dimensional nanochannel device manufactured by the process shown in FIGS. 3A-3G; FIG. 8 is an SEM photograph of FIG. 7 which is magnified to four times In FIG. 7, it is shown that the sizes on the X-Y plane and the X-Z plane are shrunken, and in FIG. 8, it is shown that a position (pointed by the arrow) where the condensed channel has the smallest size has a size at the nanometer level.

The following describes multiple simulation experiments to verify the effects described in the disclosure.

Simulation experiments

Simulation voltage: 10 Vp-p

Simulation frequency: 10 kHz

Configured channel width: 500 μm

Figure 9:
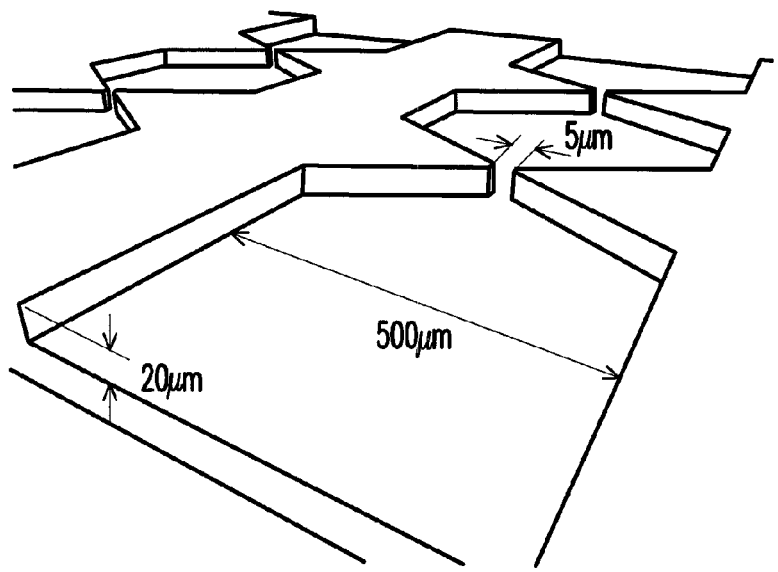
FIG. 9 is a channel device of a comparative embodiment.

Comparative embodiment: when the channel device only has a reduction in size on the X-Y plane, as shown in FIG. 9, a dielectrophoretic force in the X direction ($F_{DEP-X}$) equals 8 fN, and a dielectrophoretic force in the Y direction ($F_{DEP-y}$) equals 8 fN.

Figure 10:
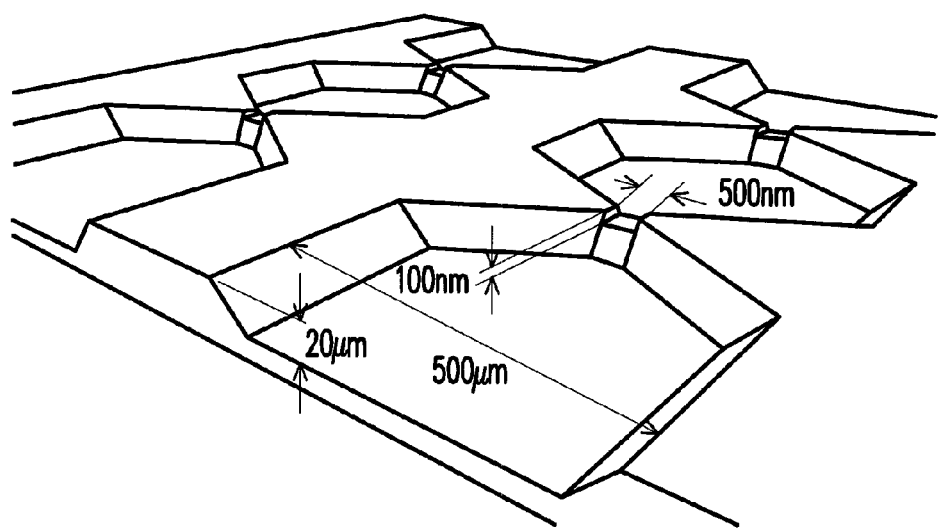
FIG. 10 is a three-dimensional nanochannel device of an experimental embodiment.

Experimental embodiment: however, for a device which utilizes the three-dimensional nanochannel device according to the disclosure (as shown in FIG. 10), not only does $F_{DEP-X}$ reach 800 fN and $F_{DEP-y}$ reach 800 fN, an effect of having a dielectrophoretic force in the Z direction ($F_{DEP-y}$) of 80 fN is also achieved since there is also an electric field gradient on the X-Z plane.

In summary, compared with conventional dielectrophoresis technologies, the disclosure not only further includes the condensation structure in the Z direction, so that condensation of the electric field is more efficient, but also omits the use of expensive nanoprocess technologies. By using technologies such as polymer rollover, a condensed electric field that reaches $10^7$ V/m is able to be generated. More importantly, the three-dimensional structure increases the reactive volume to the nanoliter level, so that a sufficient number of molecules is provided for detection.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A three-dimensional nanochannel device, comprising: a first substrate, a second substrate, and a channel layer, and the channel layer is sandwiched by the first substrate and the second substrate, wherein
   at least one channel is constituted by the first substrate, the second substrate, and the channel layer,
   the channel includes a fluid inlet, a fluid outlet, and at least one condensed channel between the fluid inlet and the fluid outlet, wherein the condensed channel at least has a first size and a second size on an X-Y plane and has a third size and a fourth size on an X-Z plane, and
   a difference between the first size and the second size is about at least two orders in scale, and a difference between the third size and the fourth size is about at least two orders in scale.

2. The three-dimensional nanochannel device as claimed in claim 1, wherein the first size is larger than the second size.

3. The three-dimensional nanochannel device as claimed in claim 1, wherein the third size is larger than the fourth size.

4. The three-dimensional nanochannel device as claimed in claim 1, wherein a surface of the first substrate, the second substrate, and the channel layer is composed of an insulation layer.

5. The three-dimensional nanochannel device as claimed in claim 1, wherein a sidewall of the channel layer is sloped.

6. The three-dimensional nanochannel device as claimed in claim 1, further comprising a first electrode and a second electrode which are respectively disposed on the first substrate and on the insulation layer of the channel layer at the fluid inlet and the fluid outlet in a direction perpendicular to the channel.

7. The three-dimensional nanochannel device as claimed in claim 1, wherein a profile of the condensed channel on the X-Y plane is reduced and then a profile of the condensed channel on the X-Z plane is reduced.

8. The three-dimensional nanochannel device as claimed in claim 1, wherein a profile of the condensed channel on the X-Z plane is reduced and then a profile of the condensed channel on the X-Y plane is reduced.

9. The three-dimensional nanochannel device as claimed in claim 1, wherein a profile of the condensed channel on the X-Y plane and a profile of the condensed channel on the X-Z plane are reduced simultaneously.

10. The three-dimensional nanochannel device as claimed in claim 1, wherein the condensed channel is located between the channel layer and the second substrate.

11. The three-dimensional nanochannel device as claimed in claim 1, wherein the condensed channel is located between the channel layer and the first substrate.

12. The three-dimensional nanochannel device as claimed in claim 1, wherein the condensed channel is located in the channel layer.

13. The three-dimensional nanochannel device as claimed in claim 1, wherein a profile of the condensed channel on the X-Y plane and a profile of the condensed channel on the X-Z plane are reduced from a micrometer level to a nanometer level.

14. The three-dimensional nanochannel device as claimed in claim 1, wherein a profile of the condensed channel on the X-Y plane and a profile of the condensed channel on the X-Z plane are reduced from a millimeter level to a micrometer level.

* * * * *